United States Patent
Eckerbom et al.

(10) Patent No.: US 7,629,039 B2
(45) Date of Patent: Dec. 8, 2009

(54) AIR GAS ANALYZER WINDOW AND A METHOD FOR PRODUCING SUCH A WINDOW

(75) Inventors: Anders Eckerbom, Vaxholm (SE); Robert Zyzanski, Stockholm (SE)

(73) Assignee: Phasein AB, Danderyd (SE)

( * ) Notice: Subject to any disclaimer, the term of this patent is extended or adjusted under 35 U.S.C. 154(b) by 551 days.

(21) Appl. No.: 10/554,393

(22) PCT Filed: Apr. 22, 2004

(86) PCT No.: PCT/SE2004/000617

§ 371 (c)(1),
(2), (4) Date: Oct. 24, 2005

(87) PCT Pub. No.: WO2004/096043

PCT Pub. Date: Nov. 11, 2004

(65) Prior Publication Data

US 2006/0251903 A1    Nov. 9, 2006

(30) Foreign Application Priority Data

Apr. 25, 2003    (SE)    ................................. 0301218

(51) Int. Cl.
*B32B 1/00* (2006.01)
*B32B 3/00* (2006.01)
*B32B 3/02* (2006.01)
*A61B 5/08* (2006.01)

(52) U.S. Cl. ................... 428/174; 428/156; 428/64.1; 600/532; 600/538

(58) Field of Classification Search ................ 428/172, 428/174, 66.3, 64.1, 156; 128/205.23, 204.23; 600/532, 538
See application file for complete search history.

(56) References Cited

U.S. PATENT DOCUMENTS

| | | | |
|---|---|---|---|
| 5,067,492 A * | 11/1991 | Yelderman et al. | 600/532 |
| 5,693,944 A | 12/1997 | Rich | |
| 6,216,692 B1 | 4/2001 | Todokoro et al. | |
| 6,806,100 B1 * | 10/2004 | Xu et al. | 438/8 |

OTHER PUBLICATIONS

Patent Abstracts of Japan vol. 011, No. 114 Apr. 10, 1987 & JP 61258718 A (Matsushita Electric IND Co Ltd), Nov. 17, 1986 abstract.

* cited by examiner

*Primary Examiner*—David R Sample
*Assistant Examiner*—Catherine Simone
(74) *Attorney, Agent, or Firm*—Young & Thompson

(57) ABSTRACT

A window for use in an adapter for an IR gas analyser for analysing breathing gases, where the gases flow through a through-penetrating passageway in the adapter, which includes windows disposed on opposite sides of the passageway so as to enable an IR beam to be sent through the windows and through the passageway containing said breathing gases. Each window is a one-piece structure comprised of plastic material and has a round basic shape that includes a surrounding edge and a central part which is sunken in relation to the surrounding edge and which forms the window through which the IR beams or rays shall be able to pass. A method of producing such a window, by injection moulding a thermoplastic material in a mould where injection of the plastic material is also disclosed.

20 Claims, 6 Drawing Sheets

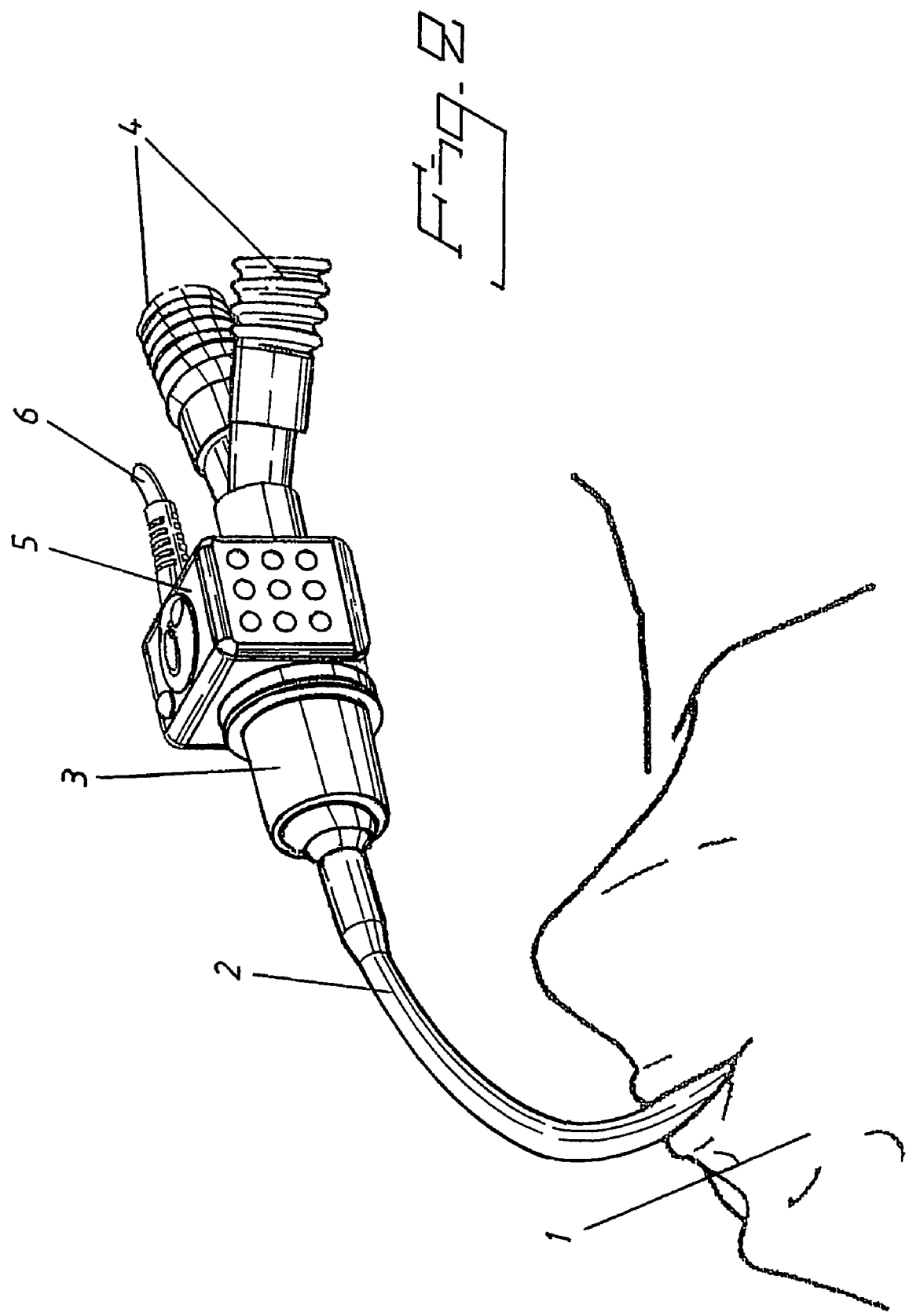

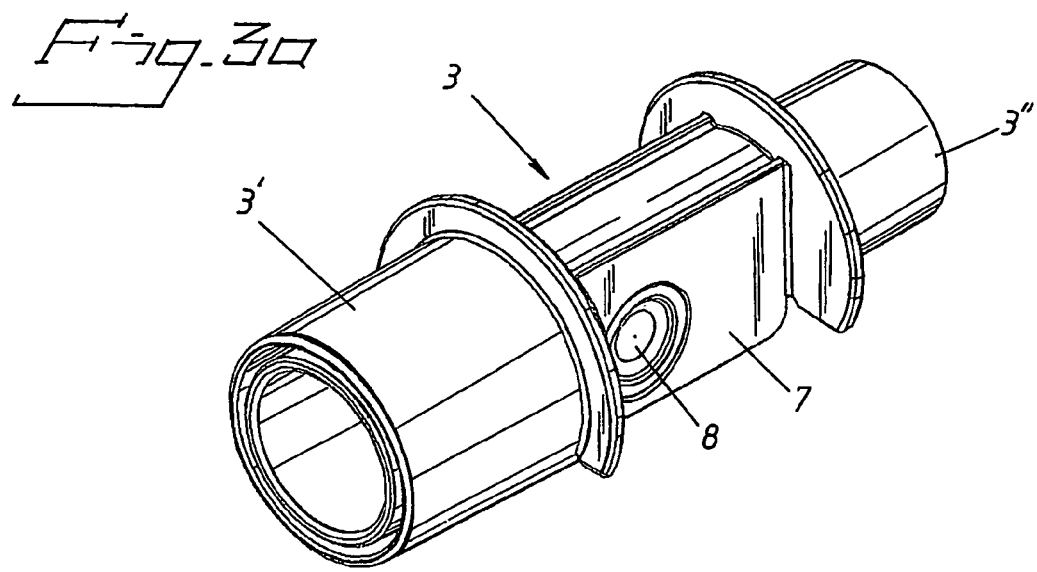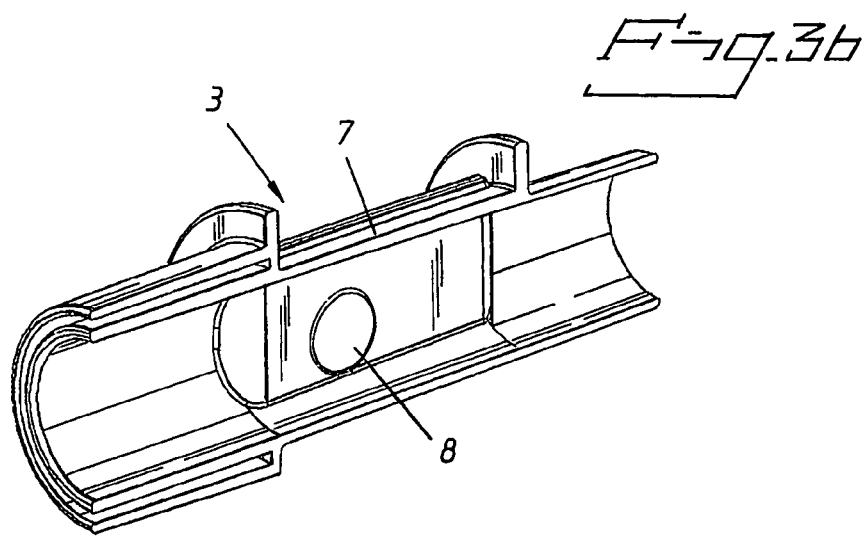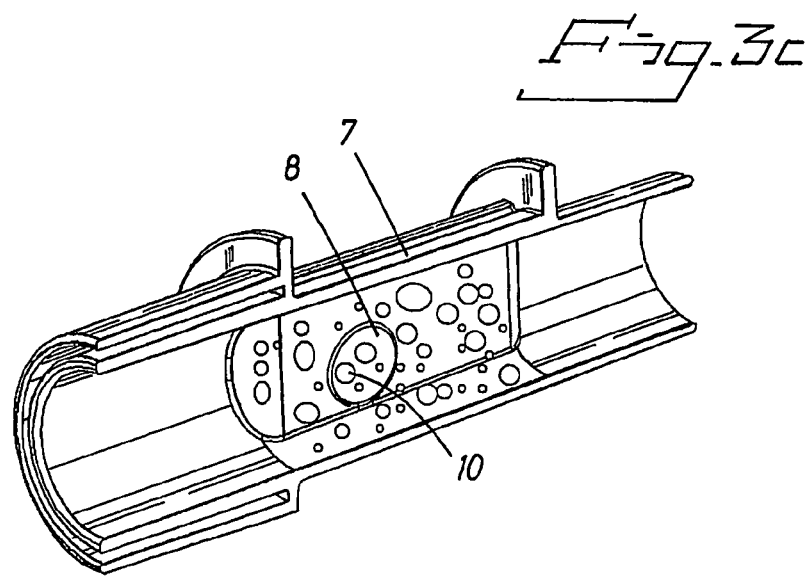

AIR GAS ANALYZER WINDOW AND A METHOD FOR PRODUCING SUCH A WINDOW

BACKGROUND OF THE INVENTION

1. Field of the Invention

Figure 1A:
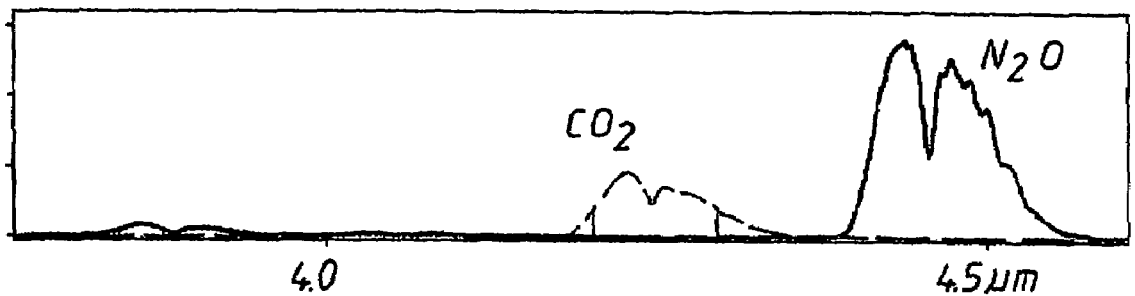

The present invention relates to an IR gas analyser window for particular use with an adapter of an IR gas analyser for the analysis of respiratory gases. The invention also relates to a particular method of producing such a window.

2. Description of the Related Art

Main flow measuring gas analysers calculate the composition of the respiratory gases of a patient, by sending infrared light through the respiratory tract of the patient and therewith measuring the absorption of said light at chosen wavelengths. For the sake of accuracy, main flow measuring gas analysers are placed as close as possible to the patient's mouth.

In order to enhance the efficiency of such respiratory gas measuring processes, there has recently been adopted the use of adapters that are inserted in the respiratory circuit and through which the respiratory gases are allowed to pass, while, at the same time, coupling a measuring instrument to the adapter for registering the gases that pass therethrough.

A gas analyser adapter is known from, for instance, the International Patent Application PCT/SE02/01528 (Publication No. WO 03/017837). This adapter is intended for coaction with a measuring head known from the International Patent Application PCT/SE02/01946 (Publication No. WO 03/060490). The adapter includes a window which constitutes a delimitation of a gas passageway through which the gas to be analysed flows, and the analysis is effected by sending a beam of infrared light through a window on one side of the gas passageway and further through the gas present in said passageway, and through a corresponding window on the other side of the gas passageway, where said beam is received by an IR detector.

Similar adapters are known, for instance, from U.S. Pat. Nos. 5,616,923; 6,095,986; 6,216,692; and 6,258,040.

A particular problem that has been observed in respect of the aforesaid types of adapter resides in the moisture deposits that can occur on the inside of the adapter walls. These deposits are due to the fact that the respiratory gases contain a great deal of moisture and because the moisture contained condenses inside the adapter due to the difference in temperature between the respiratory gas present in the adapter and the considerably colder ambient air on the outside of the adapter, wherein said moisture is deposited in water droplet form, inter alia on the windows in the adapter.

The windows through which the IR rays shall pass have been found to be a problematic source in those adapters of the aforesaid kind known hitherto. The requirements that should preferably be placed generally on the windows included in adapters of the aforesaid kind are:

That the windows shall allow IR rays to pass through in the desired wavelength range.

That the windows shall positively eliminate any condensation problems emanating from the gases in the respiratory circuit.

That the windows shall not be deformed by mechanical action or as a result of pressure changes in the respiratory circuit.

That surface collection of liquid shall be counteracted.

That the windows can be mounted in the adapter in a gas-tight manner.

That the windows have a low production cost.

That it shall be possible to mount the windows in the adapter in a simple and inexpensive manner.

The following problems have been observed among the various solutions proposed with regard to window designs:

Traditional gas windows are expensive and often need to be heated in order to avoid moisture deposits. Heating has the additional disadvantage of utilising power and also lengthens the time before which the sensor can begin to be used. Heating also results in different material compositions that make recovery of the adapters used difficult to achieve.

Foils that are sufficiently strong mechanically normally have a poor transmission capacity in high wavelength regions. It has also been found difficult to flatten foil, therewith requiring some form of stretching or tensioning means, which, in turn, renders the elements twist responsive. Normally, additional fastener elements are required to mount the foils flush with the inner wall, so as to prevent the formation of pockets that are able to collect liquid around the window. It is often also necessary to glue these additional fastener elements, in order to obtain a secure and tight fastening.

The different component parts and the mounting steps involved make manufacture of the product expensive. As mentioned above, the use of different materials also results in recovery problems.

BRIEF SUMMARY OF THE INVENTION

Accordingly, the object of the present invention is to provide a novel window for gas analysers of the aforesaid kind with which the above described problems and drawbacks associated with windows of this kind known hitherto are avoided.

This object of the invention is achieved with a window of the aforesaid kind which is formed in one piece from a plastic material and which has a round basic shape with a surrounding or peripheral edge and a central part which is sunken in relation to said edge and which forms the window through which the IR rays shall be able to pass.

According to one preferred embodiment, the central part of said window is arched somewhat away from the surrounding edge.

According to another preferred embodiment of the invention, the window is comprised of a plastic material of the same kind as that used for the adapter in which the window shall be mounted.

According to another preferred embodiment of the invention, the window is designed to enable it to be fastened in the adapter by means of gluing, ultrasound welding or heat welding.

The aforesaid window design solution provides a window of particular construction suitable for injection moulding. However, it has not earlier been possible to injection mould such a window of sufficient thinness, about 80-90 $\mu$m, and uniform material thickness in that part of the window through which the major part of the IR rays shall pass. Traditional injection moulding methods easily result in deficient levelling of the thin section, which has limited the minimum thickness to about 250-300 $\mu$m. Other production methods, such as die embossing enable the thickness to be brought down to about 150-200 $\mu$m. However, in order to achieve satisfactory transmission properties, it is necessary for the thin section of the window thickness to be at most 90 $\mu$m. Accordingly, a further object of the present invention is to provide a method of producing such a window.

This further object of the invention is achieved by a window manufacturing method in which the window is formed by injection moulding a thermoplastic material in a mould where said plastic material is injected into the mould centrally in the middle of the ultimate or forthcoming window.

According to one preferred embodiment of said inventive method, a surface tension modifying substance is admixed with the plastic material prior to the injection moulding process.

According to another preferred embodiment of the inventive method, injection moulding is carried out in a preheated mould tool.

BRIEF DESCRIPTION OF THE DRAWING FIGS.

Figure 1B:
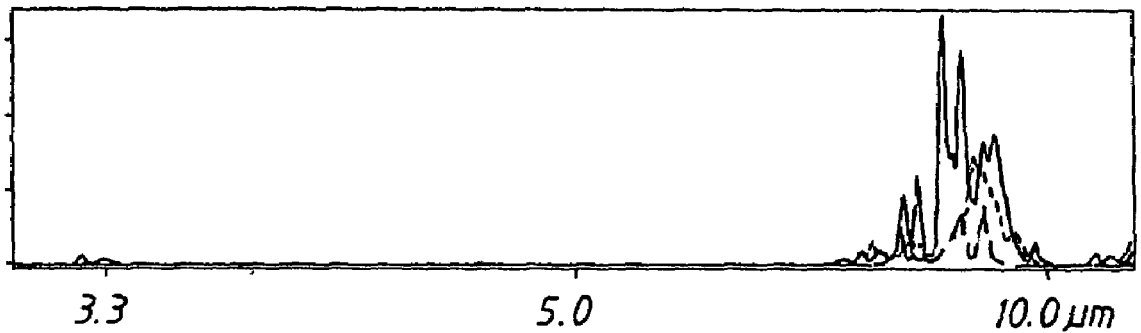
Figure 1C:
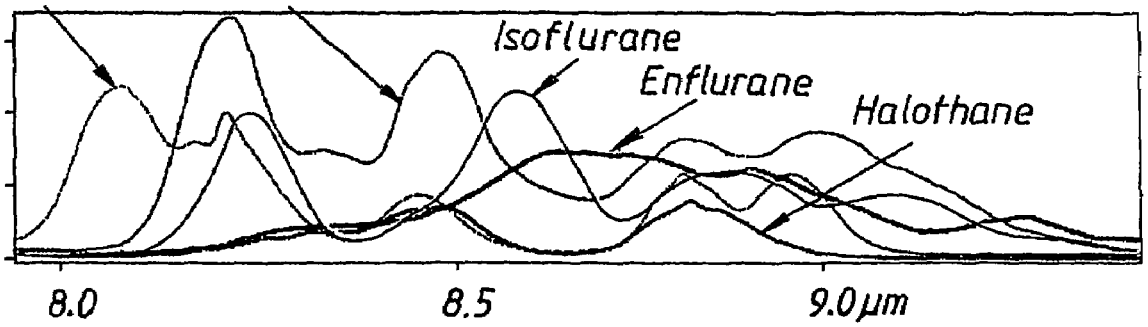
Figure 4A:
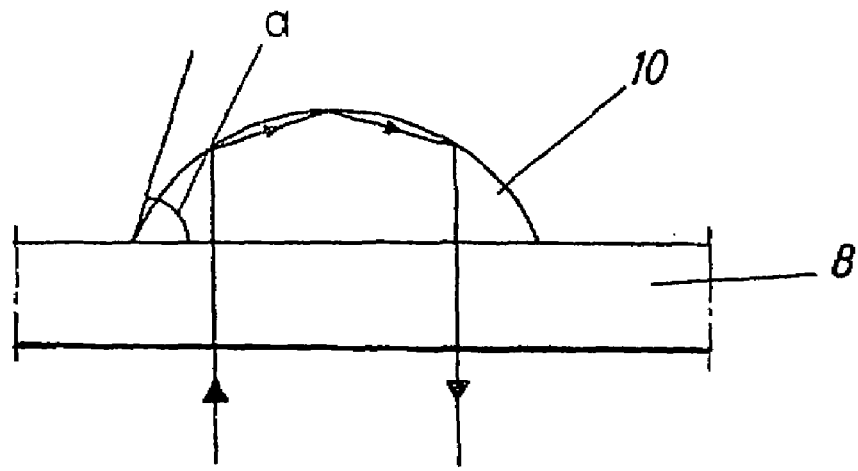
Figure 4B:
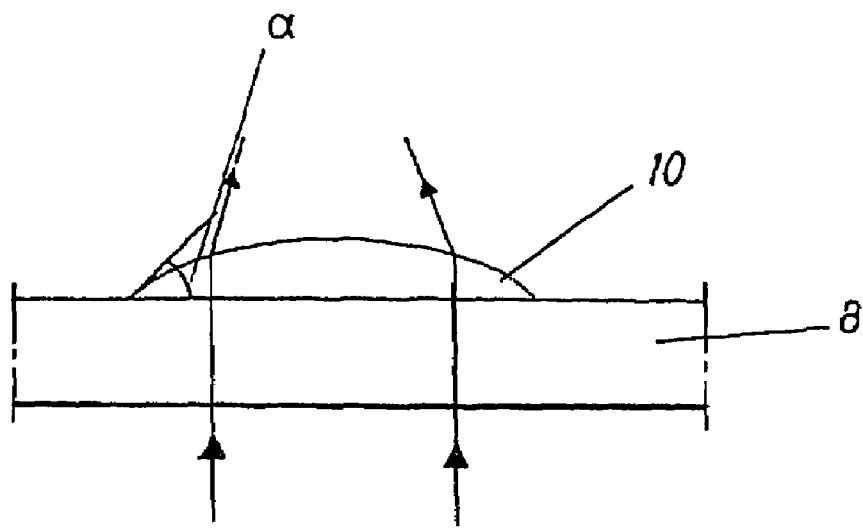
Figure 5A:
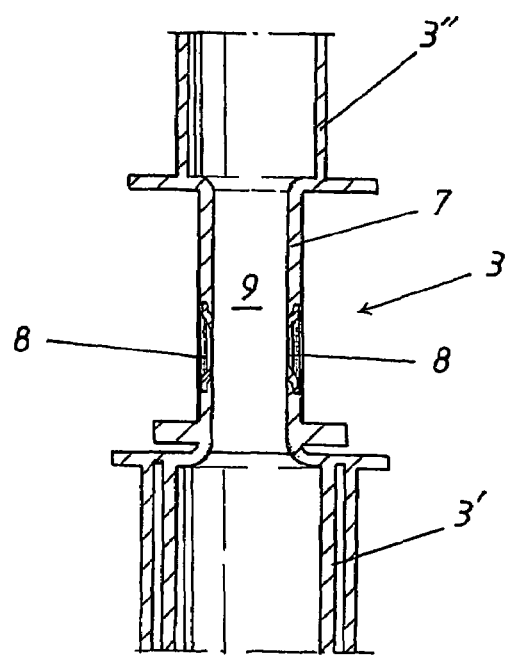
Figure 5B:
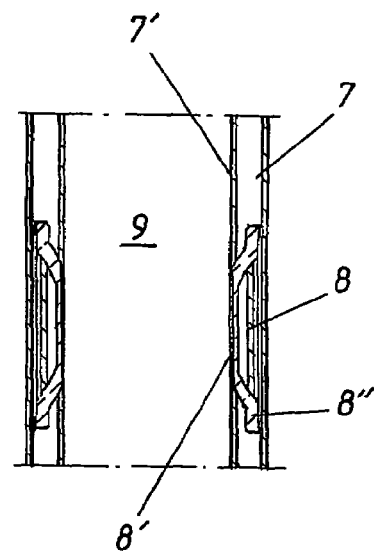
Figure 6:
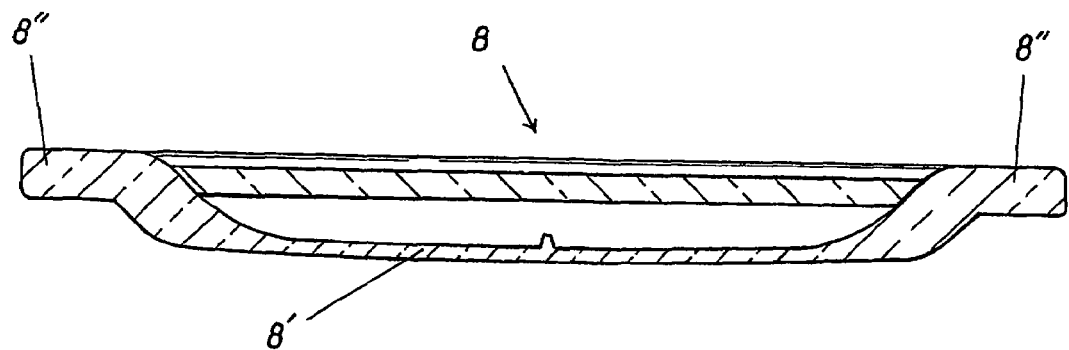
Figure 7:
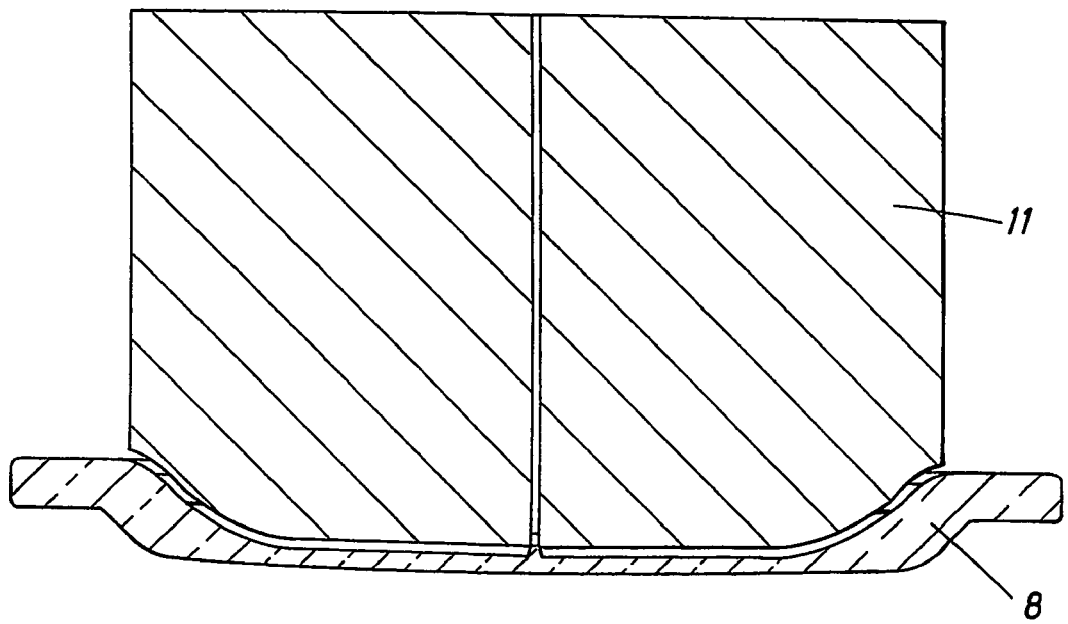
Figure 8:
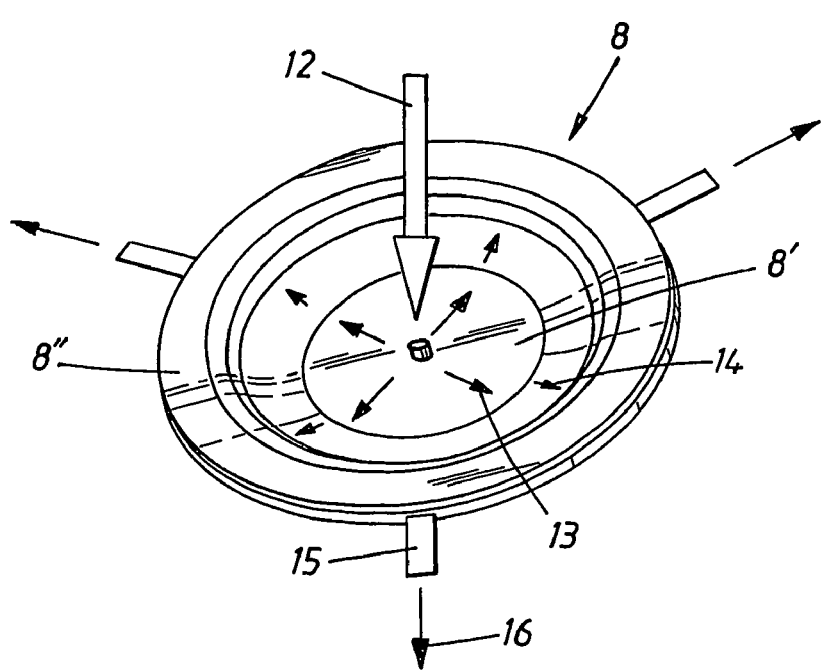

The invention will now be described in more detail with reference to a pair of non-limiting embodiments illustrated in the accompanying drawings, of which FIG. 1 illustrates the IR-absorption spectrum of different gases measured by a gas analyser, more specifically in FIG. 1a the IR-absorption spectrum for $CO_2$ and $N_2O$, in FIG. 1b the IR-absorption spectrum for anaesthetic gases, and in FIG. 1c the IR-absorption spectrum for separate anaesthetic gases in the wavelength region of 8-9.5 μm; FIG. 2 is a principle illustration of a patient breathing via a gas analyser; FIG. 3a is a perspective view of a gas analyser adapter; FIG. 3b is a longitudinal perspective view of an adapter according to FIG. 3a; FIG. 3c is a perspective longitudinal sectioned view of an adapter according to FIG. 3a with water droplets (mist) inside the adapter; FIG. 4a illustrates schematically the path of the rays in respect of a water droplet of larger contact angle FIG. 4b illustrates a corresponding ray or beam path in the case of a water droplet of slightly smaller contact angle; FIG. 5a is a longitudinally sectioned view of a gas analyser adapter for a window constructed in accordance with the invention; FIG. 5b illustrates part of the longitudinal section shown in FIG. 5a in larger scale, namely the parts of a centre section of the adapter that includes windows according to the present invention; FIG. 6 is a cross-sectional view of an inventive window, shown in a much larger scale; FIG. 7 illustrates part of an injection moulding nozzle and a window, both in cross-section, in the manufacture of the window; and FIG. 8 is a schematic illustration of the course taken in moulding of the window in accordance with the inventive method.

DETAILED DESCRIPTION OF THE PREFERRED EMBODIMENTS

As before mentioned, FIG. 1 illustrates IR light absorption spectra in respect of the analysis of respiratory gases with the aid of an IR gas analyser. As will be seen from FIG. 1a, the absorption spectra of $CO_2$ and $N_2O$ lie in the region of 4-4.5 μm, which is the region in which windows used hitherto exhibit good transmittance. In distinction, the windows used hitherto have poor transmittance in the region of 8-10 μm, which, as evident from FIG. 1b, is the region where the best absorption peaks for anaesthesia gases are found. FIG. 1c illustrates more specifically the absorption spectrum of the most common anaesthesia gases, from which it will be clearly seen that these absorption spectra are mainly found in the region of 8-9.5 μm. Accordingly, an object of the present invention has been the provision of a window which will provide good transmittance also at these wavelengths of the infrared light.

FIG. 2 illustrates the general principle of how respiratory gases to/from a patient are analysed. The patient 1 breathes via a hose 2 which is connected to an adapter 3. Connected to the adapter 3 are respirator hoses 4 that are responsible for the supply of air/breathing gas to/from the patient 1. The adapter 3 is fitted with a measuring head 5, for instance of the kind described in the aforesaid PCT/SE02/01946, said measuring head 5 containing electronics for the emission of infrared light and the analysis of the infrared light received, and is connected to a signal cable 6 for conducting the results to a registration/indicating device, for instance a personal computer. The adapter 3 includes the windows that are the subject of the present invention and through which the infrared light passes in the measuring head 5.

As will be evident from FIG. 3a, the adapter 3 has two ends 3' and 3" that carry respective connections for the patient hose 2 and the respirator hose 4. The adapter also includes a centre part 7 to which the measuring head 5 can be fitted and in which the inventive windows 8 are provided. Extending through the adapter is a through-penetrating passageway 9 that leads the breathing gases from the patient hose 2 to the respirator hose 4, and vice versa. Two windows 8 are disposed opposite one another in the centre part 7, so that IR rays sent through one window 8 by the measuring head 5 will pass through the passageway 9 containing the breathing gases and out through the other window 8 on the other side of the centre part 7. FIG. 3b illustrates the ideal case in which no water droplets precipitate in the passageway 9, whereas FIG. 3c illustrates the case in which water droplets 10 precipitate in the passageway 9 and also settle on the inner surface of the window 8.

The problems caused by water droplets that settle on the inner surface of the window 8 will be described with the aid of FIG. 4. If no measures to prevent/reduce the build-up of water droplets on the inside of window 8 a large water droplet 10 forms on the inside of said window, as illustrated in FIG. 4a, and a relatively large contact angle will be obtained between the window 8 and the water droplet 10, resulting in a relatively large angle of incidence of an incident ray on the surface of said droplet, with the subsequent reflection of the entire ray. This thus prevents the infrared light ray from passing through the through-penetrating passageway in the adapter, therewith making it impossible to effect any measurement. On the other hand, if measures have been taken to prevent/reduce the formation of water droplets on the inside of the window, as in the FIG. 4b illustration, the contact angle between the window 8 and the water droplet 10 will be relatively small, wherewith the angle of incidence of an incident ray against the surface of the water droplet will also be relatively small and the ray is able to pass the surface of said droplet 10 with only small refraction and pass through the through-penetrating passageway containing the gas to be analysed, and consequently exit through the window on the opposite side of the passageway and allow the gas to be measured and analysed.

Purely technically, the formation of droplets on the inside of a plastic window is explained by the difference in surface tension between the plastic surface and the water. Traditional polyolefins are highly hydrophobic, wherein the droplets that form obtain a large contact angle. The difference in surface tension between the plastic surface and the water can be eliminated by adding a surface tension modifying agent, wherewith the contact angle is reduced towards zero and the water is dispersed as a uniform film over the plastic surface. In order for a surface tension modifying substance to function, it must be present on the surface of the polymer and also be at least slightly soluble in water. Those surface tension modifying agents used have this property and function so that the surface tension modifying substance present in the polymer migrates towards the plastic surface where said substance decreases on the actual surface by dissolving in the water present on said surface, therewith achieving automatic replenishment of the surface tension modifying substance so that a generally constant proportion of said substance is on hand on the plastic surface. Typical concentrations of such surface tension modifying substances are 1-3%.

FIG. 5a is a longitudinally sectioned view of an adapter 3 which includes an inventive window in two mutually opposing walls of the centre part 7 of the adapter. FIG. 5b illustrates a portion of the adapter centre part 7, more particularly the portion in which the windows are disposed in the walls of said centre part 7, whereas FIG. 6 illustrates a window 8 in larger scale.

In accordance with the invention, the window 8 is formed as a one-piece structure from plastic material and has a round basic shape, so as to simplify manufacture and mounting of the window. The window has a surrounding outer edge 8" and a central part 8' which is sunken in relation to the edge 8" and which constitutes the translucent part of the window. The central part 8' will preferably have a size of about 80-90 μm, so as to provide good transmission throughout the entire desired wavelength range of 4-10 μm. The surrounding edge 8" is suitably several times thicker than the central part 8', e.g. with a thickness of about 1 mm, partly to provide a stable window and partly to facilitate handling of the window 8 when fitting the same to an adapter 3. The central part 8' of the window is also suitably caused to arch slightly away from the surrounding outer edge 8", so as to allow moisture collecting on the window to run off more easily. The window will conveniently have a gradual transition from the thicker surrounding edge 8" towards the thinner central part 8'. This results in a stronger window, which is also easier to injection mould.

As will be seen from FIG. 5b, the window 8 is mounted on the centre part 7 of the adapter wall, wherein the centre part 7 is given in manufacture an opening that includes a ledge which facilitates fitting of the window 8. The window 8 and the wall opening are conveniently dimensioned so that the centre part 8' of the window will lie generally flush with the inner wall surface 7' of the centre part, such as to avoid the formation of liquid-collecting pockets between the window 8 and the inner wall surface 7' or to avoid the occurrence of turbulent flows in the through-penetrating passageway 9. When the central part 8' of the window is also arched so as to bulge slightly into the passageway, i.e. slightly beyond the surface of the inner wall surface 7', the runoff of any moisture on the window is also facilitated.

The window 8 is suitably made of a polyolefin, which can be readily injection moulded, for instance a polyethylene and then preferably an HD polyethylene. The adapter 3 itself may consist of an injection moulded polyolefin therewith constructing the adapter as a whole, including the window, of one and the same material, which facilitates recovery of the material and constitutes good material selection from an environmental aspect.

The runoff of water from the window 8 can be facilitated by conveniently treating the window with a surface tension modifying substance that will prevent the build-up of large water droplets, such as the droplets shown in FIG. 4a, on the inside of the window. A surface tension modifying substance may conveniently be included in the material from which the window is made, so as to avoid the need of further treating the window subsequent to its manufacture.

A window 8 of the aforedescribed design can be readily fastened in the adapter, for instance by gluing or preferably by ultrasound or heat welding.

As before mentioned, an inventive window is suitably produced by injection moulding. Traditional injection moulding of such a product, using an ingate or a sprue at one end of the mould, can easily result in deficient spread or levelling of that part of the window that shall form the central part 8' thereof, since the spacing between the two mould halves would be very small when the product shall have a thickness solely in the order of 80-90 μm. This would result in a large number of scrapped windows that are perforated or uneven in the central part of the window.

Accordingly, the invention also relates to a particular method of producing a window according to the invention. According to the method, the window is injection moulded from a thermoplastic substance in a mould where said substance is injected centrally into the centre of the mould, i.e. in the centre of the ultimate or forthcoming window. This is illustrated schematically in FIG. 7, which shows a window 8 according to the invention and a part of the injection moulding nozzle 11 used to inject the thermoplastic material into the mould. The mould itself has been excluded from the figure, since the mould has no great importance with regard to the invention. FIG. 8 illustrates schematically how the injected thermoplastic material flows centrally in towards the centre of the bottom of the ultimate window 8, as indicated by the arrow 12. As indicated by the arrows 13, the plastic material then flows radially outwards to form the central part 8' of the window 8, and then outwards in the direction of the arrows 14 towards the surrounding edge 8". The injection mould also includes air vents 15, which extend from that part of the mould forming the surrounding edge 8" and through which air can be evacuated from the mould cavity.

In order to prevent the injected thermoplastic material from solidifying in that part of the mould in which the central window part 8' shall be formed, the mould is suitably heated so that the plastic material will flow out more easily and also fill that part of the mould that shall form the surrounding edge. Preheating of the mould is suitably controlled so that, during the injection process, the temperature will be at its highest in the central part of the mould cavity and then decrease gradually towards the outer part of the mould cavity.

The volume of air enclosed in the mould cavity can be evacuated through the radially extending air vents 15, as indicated by the arrows 16.

In the case of injection moulding of precision elements, such as the inventive windows, it is essential that the temperature of the mould cavity and the ingate or sprue can be controlled very accurately during the injection process. A temperature which is too low will result in incomplete filling of the thin central section, whereas a temperature that is too high can result in burning of the plastic material. Practical tests have shown that a mould cavity temperature of about 80° C. and a sprue temperature of about 120° C. are suitable temperature magnitudes. In these tests, there was produced a window that had a diameter of 10 mm and a thickness of 80 μm in its centre section, while using a sprue of 0.25 mm in diameter. The three radially extending air vents had a width of 0.6 mm, a thickness of 15 μm and a length of 1.6 mm.

With the intention of effectively producing a product that preferably includes a surface tension modifying substance on its surface, it is also proposed in accordance with the present invention that such a substance is mixed with a granulated plastic material prior to injection moulding of the window, and to mould the window with said substance admixed with said granular plastic material.

Polyolefins, preferably an HD polyethylene have been preferred as the material used for injection moulding the window in accordance with the invention. A suitable surface tension modifying substance that has been found to function in admixture with the plastic granulate and for injection moulding in accordance with the inventive method are sorbitol esters and glycerol monooleates, for instance.

It will be understood that materials other than those mentioned in the aforegoing can also be used, provided that these materials have similar properties than the mentioned materials and are able to provide corresponding end products.

The invention claimed is:

1. A window for use in an adapter (3) for an IR gas analyser for the analysis of respiratory gases, where the gases flow through a through-penetrating passageway (9) in the adapter (3) with a window (8) disposed on mutually opposite sides of the passageway (9) so that an IR beam can be sent through the windows (8) and the passageway (9) containing said breathing gases, wherein the window (8) is a one-piece structure made of plastic material and having a round basic shape that includes a surrounding edge (8") and a central part (8') which is sunken in relation to said edge (8") and which constitutes the window through which the IR rays shall be able to pass, and a center part of the window (8) generally lies flush with an inner wall surface (7').

2. The window according to claim 1, wherein the plastic material is a polyolefin.

3. The window according to claim 2, wherein the plastic material is an HD polyethylene.

4. The window according to claim 1, wherein the plastic material includes a surface tension modifying substance.

5. The window according to claim 2, wherein the plastic material includes a surface tension modifying substance.

6. The window according to claim 1, wherein the window is formed by an injection moulding process.

7. The window according to claim 1, wherein the central part (8') of the window is arched in a direction away from the surrounding edge (8").

8. The window according to claim 1, wherein the window has been glued in a recess in a wall surrounding the through-penetrating passageway (9) in the adapter (3).

9. The window according to claim 1, wherein the window is fastened by ultra-soundwelding or heat-welding in a recess in a wall surrounding the through-penetrating passageway (9) in the adapter (3).

10. A method of producing a window in accordance with claim 1, comprising:

forming the window (8) by injection moulding a thermoplastic material in a mould in which injection of the plastic material into the mould is effected centrally in the centre of the ultimate or forthcoming window.

11. The method according to claim 10, further comprising: mixing a surface tension modifying substance in the thermoplastic material prior to the injection moulding process.

12. The method according to claim 10, wherein the injection moulding process is effected in a preheated mould tool.

13. The method according to claim 11, wherein the injection moulding process is effected in a preheated mould tool.

14. An adapter (3) for an IR gas analyser for the analysis of respiratory gases, comprising:

a through-penetrating passageway (9) in the adapter (3); and two windows (8) disposed on mutually opposite sides of the passageway (9) so that an IR beam can be sent through the two windows (8) and the passageway (9) containing said breathing gases, wherein each window (8) is a one-piece structure made of plastic material and having a round basic shape that includes a surrounding edge (8") and a central part (8') which is sunken in relation to said edge (8") and which constitutes the window through which the IR rays shall be able to pass, and a center part of each window (8) generally lies flush with an inner wall surface (7').

15. The adapter (3) according to claim 14, wherein the plastic material is a polyolefin.

16. The adapter (3) according to claim 14, wherein the plastic material includes a surface tension modifying substance.

17. The adapter (3) according to claim 14, wherein each window is formed by an injection moulding process.

18. The adapter (3) according to claim 14, wherein the central part (8') of each window is arched in a direction away from the surrounding edge (8").

19. The adapter (3) according to claim 14, wherein each window has been glued in a recess in a wall surrounding the through-penetrating passageway (9) in the adapter (3).

20. The adapter (3) according to claim 14, wherein each window is fastened by ultra-soundwelding or heat-welding in a recess in a wall surrounding the through-penetrating passageway (9) in the adapter (3).

* * * * *

UNITED STATES PATENT AND TRADEMARK OFFICE
CERTIFICATE OF CORRECTION

PATENT NO. : 7,629,039 B2 Page 1 of 1
APPLICATION NO. : 10/554393
DATED : December 8, 2009
INVENTOR(S) : Eckerbom et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 954 days.

Signed and Sealed this

Twenty-first Day of December, 2010

David J. Kappos
*Director of the United States Patent and Trademark Office*